United States Patent [19]

Ward, III et al.

[11] E Patent Number: Re. 33,452

[45] Reissued Date of Patent: Nov. 20, 1990

[54] METHOD FOR MAKING ALKYLHALOSILANES

[75] Inventors: William J. Ward, III, Schenectady; Alan Ritzer, Sand Lake; Kenneth M. Carroll, Albany; John W. Flock, Schenectady, all of N.Y.

[73] Assignee: General Electric Company, Schenectady, N.Y.

[21] Appl. No.: 911,614

[22] Filed: Sep. 25, 1986

Related U.S. Patent Documents

Reissue of:

[64] Patent No.: 4,500,724
Issued: Feb. 19, 1985
Appl. No.: 518,236
Filed: Jul. 28, 1983

[51] Int. Cl.[5] ..... C07F 7/04

[52] U.S. Cl. ..... 556/472; 252/184; 252/192; 502/113; 502/225; 502/343

[58] Field of Search ..... 556/472; 252/182, 184, 252/192; 502/113, 225, 343

[56] References Cited

U.S. PATENT DOCUMENTS

| | | | |
|---|---|---|---|
| 2,380,995 | 8/1945 | Rochow . | |
| 2,380,996 | 8/1945 | Rochow et al. | 556/472 |
| 2,380,997 | 8/1945 | Patnode . | |
| 2,383,818 | 8/1945 | Rochow et al. . | |
| 2,389,931 | 11/1945 | Reed et al. . | |
| 2,427,605 | 9/1947 | Hurd . | |
| 2,443,902 | 6/1948 | Ferguson et al. . | |
| 2,464,033 | 3/1949 | Gilliam . | |
| 2,466,412 | 4/1949 | Gilliam et al. . | |
| 2,657,114 | 10/1953 | Wagner . | |
| 2,666,775 | 1/1919 | Nitzsche . | |
| 2,666,776 | 1/1919 | Nitzsche . | |
| 2,865,939 | 12/1958 | Little et al. | 556/472 |
| 2,877,254 | 3/1959 | Enk et al. . | |
| 2,887,502 | 5/1959 | Bluestein | 556/472 |
| 2,903,473 | 9/1959 | Takami et al. | 556/472 |
| 2,917,529 | 12/1959 | Drysdale . | |
| 3,069,452 | 12/1962 | Rossmy . | |
| 3,133,109 | 5/1964 | Dotson . | |
| 3,446,829 | 5/1969 | Zock . | |
| 3,555,064 | 1/1971 | Turetskaya et al. | 556/472 |
| 4,307,242 | 12/1981 | Shah et al. | 556/472 |
| 4,314,908 | 2/1982 | Downing et al. . | |
| 4,450,282 | 5/1984 | Ritzer et al. | 556/472 |
| 4,487,950 | 12/1984 | Ward et al. | 556/472 |

FOREIGN PATENT DOCUMENTS

| | | | |
|---|---|---|---|
| 5351193 | 5/1978 | Japan | 556/472 UX |
| 1197720 | 7/1970 | United Kingdom | 556/472 U X |
| 1235461 | 6/1971 | United Kingdom | 556/472 U X |

OTHER PUBLICATIONS

Voorhoeve, "Organohalosilanes: Precursors to Silicanes", Elsevier Publishing Co., Amsterdam, Holland, pp. 127, 135, 229, 230 (1962).

"J. of Appl. Chem. of USSR", pp. 2245–2249, 49, vol. 10, pp. 2236–2240 (1976).

Potrov, "Synthesis of Organosilicon Monomers", Consultants Bureau, N.Y., pp. 31, 32, 39–40, 43 (1964).

"Advances in Inorg. & Radiochem.", 6; pp. 383–432 (1964).

"Zh. Obstrch. Khim.", 42, pp. 1516–1520 (1972).

Eaboue et al., "Synthesis and Reactions of the Si–C Bond", Organometallic Compounds of the Group II Element: vol. 1, The Bond to Carbon, pp. 188–205, (1968).

Influence of Some Admixtures on the Activity of Contact Masses for Direct Synthesis of Methyl Chlorosilanes, by Radiosavlyevich et al, Institute of Inorganic Chemistry, Dept. of Technology, Yugoslavia (1965).

*Primary Examiner*—Paul F. Shaver

*Attorney, Agent, or Firm*—James Magee, Jr.; James C. Davis, Jr.

[57] ABSTRACT

A method is provided for making alkylhalosilanes by effecting reaction between an alkyl halide, such as methyl chloride and powdered silicon in the presence of a copper-zinc-tin catalyst. Significant improvements in reaction rate and product selectivity are achieved when copper is employed at a critical weight percent relative to silicon and critical weight ratios of tin and zinc are employed relative to copper.

32 Claims, No Drawings

METHOD FOR MAKING ALKYLHALOSILANES

Matter enclosed in heavy brackets [ ] appears in the original patent but forms no part of this reissue specification; matter printed in italics indicates the additions made by reissue.

CROSS REFERENCE TO RELATED APPLICATIONS

Reference is made to the copending application of Ward et al, Ser. No. 456,470, filed Jan. 7, 1983, for Method for Making Methylchlorosilanes, and copending application of Ritzer et al, Ser. No. 288,175, filed July 29, 1981, for A Catalyst for a Process for Producing Silanes, where both applications are assigned to the same assignee as the present invention and incorporated herein by reference.

BACKGROUND OF THE INVENTION

The present invention relates to a method for making alkylhalosilanes. More particularly, the present invention relates to a process involving the reaction of methyl chloride and powdered silicon in the presence of a copper-zinc-tin catalyst.

Prior to the present invention, methylchlorosilanes were made by effecting reaction between powdered silicon and methyl chloride in the presence of a copper catalyst, as shown by U.S. Pat. No. 2,380,995, Rochow, assigned to the same assignee as the present invention. Improved results were achieved by utilizing a fluidized bed reactor, as shown by Reed et al, U.S. Pat. No. 2,389,931, also assigned to the same assignee as the present invention. Further improvements in the production of particular methylchlorosilanes were achieved when zinc was used in combination with copper catalyst as a promoter as shown by Gilliam, U.S. Pat. No. 2,464,033. Gilliam teaches that a proportion of from about 2 to about 50% by weight of copper in elemental form or as the halide or oxide, and preferably 5 to 20% and from about 0.03 to about 0.75% by weight of zinc in the form of zinc halide, zinc oxide, or zinc metal, or mixture thereof, where the weight of copper and zinc are based on the weight of silicon, can be used as a promoter for making dialkyl substituted dihalogenosilanes, such as dimethyldichlorosilane in the direct reaction between silicon powder and methyl chloride.

Subsequent to the investigation made by Gilliam, Radosavlyevich et al, found that micro quantities of silver added to contact masses resulting from the reaction of powdered silicon and methyl chloride in the presence of cuprous chloride decreased the yield of methylchlorosilanes, while tin and calcium chloride increased the rate of formation of methylchlorosilanes as reported in "Influence of Some Admixtures on the Activity of Contact Masses for Direct Synthesis of Methylchlorosilanes", Institute of Inorganic Chemistry, Belgrade, Yugoslavia, (1965).

As utilized hereinafter, the term "methylchlorosilanes" includes dimethyldichlorosilane, which is the preferred methylchlorosilane, and a variety of other silanes such as tetramethylsilane, trimethylchlorosilane, methyltrichlorosilane, silicon tetrachloride, trichlorosilane, methyldichlorosilane and dimethylchlorosilane.

In addition to the above methylchlorosilanes, "residue" is also formed during the production of methylchlorosilane crude. Residue means products in the methylchlorosilane crude having a boiling point $>70°$ C.

at atmospheric pressure. Residue consists of such materials as disilanes, for example, symmetrical 1,1,2,2-tetrachlorodimethyldisilane, 1,1,2-trichlorotrimethyldisilane, disiloxanes, disilmethylenes and other higher boiling species, for example, trisilanes, trisiloxanes, trisilmethylenes, etc. In addition to residue, those skilled in the art also are interested in T/D weight ratio of the methylchlorosilane crude. The T/D ratio is the ratio of methyltrichlorosilane to dimethyldichlorosilane in the crude methylchlorosilane reaction product. Accordingly, an increase in the T/D ratio indicates that there is a decrease in the production of the preferred dimethyldichlorosilane.

Although as taught by the prior art, while zinc or tin can be valuable promoters for copper catalyst, or copper-silicon contact mass in the reaction between powdered silicon and methyl chloride, it has been found that the rate of crude methylchlorosilane formation and the T/D ratio are often unsatisfactory.

When defining a rate constant for crude methylchlorosilane formation, the term "$K_p$", or "reaction rate constant for methylchlorosilane product" is often used by those skilled in the art. A more detailed derivation of $K_p$, is shown below immediately prior to the examples.

$K_p$ values can be obtained using an apparatus as shown by FIG. 2. On a relative scale, when a mixture of copper and powdered silicon containing 5% by weight of copper is used to make methylchlorosilane, a "$K_p$38 (grams silane/grame silicon, hr) having a numerical value of about 13 can be obtained. A $K_p$ of 16 can be obtained from a mixture of powdered silicon containing 5% by weight copper and 0.5% by weight zinc. A $K_p$ of 45 can be obtained when a mixture of powdered silicon containing 5% weight copper and 0.005% by weight tin is reacted with methyl chloride.

Although the above $K_p$ values indicate that tin promoted copper catalyst can provide a superior methylchlorosilane formation rate when used with powdered silicon and methyl chloride, it has been found that the selectivity of tin promoted copper catalyst can be inferior to zinc promoted copper catalyst.

As defined hereinafter, the term "selectivity" means the ability of a catalyst to maximize the production of dimethyldichlorosilane, as shown for example by a reduction in the value of the T/D ratio and a reduction in the % residue. It is found, for example, that although a higher $K_p$ can be obtained when tin is utilized with copper to catalyze the reaction between powdered silicon and methyl chloride, a significant increase in the T/D ratio is also effected, as compared to the use of a copper catalyst promoted with zinc.

The present invention is based on the surprising discovery that direct method reactions between powdered silicon and methyl chloride in the presence of an effective amount of a copper-zinc-tin catalyst as defined hereinafter, can provide $K_p$ values about twice that shown for tin promoted copper catalyst as discussed above, while simultaneously substantially improving the selectively over zinc promoted copper catalyst and over tin promoted copper catalyst. More particularly, optimum selectivity and maximum $K_p$ values can be obtained by practicing the direct method with a mixture of powdered silicon, copper, tin and zinc containing 0.5–10% by weight of copper, based on the weight of silicon, where the copper can be in the free state or in the form of a copper compound as defined hereinafter, with 0.01 to 0.5 part of zinc, per part of copper and 200–3,000 ppm of tin relative to copper, where both zinc and tin are also expressed in terms of weight of metal, although optionally employed as a zinc compound or a tin compound, as defined hereinafter.

STATEMENT OF THE INVENTION

There is provided by the present invention, a method for making methylchlorosilanes which substantially enhances the rate of dimethyldichlorosilane formation, while substantially reducing the weight ratio of methyltrichlorosilane to dimethyldichlorosilane, and maintaining or reducing the percent by weight of products in the resulting methylchlorosilane crude having a boiling point of greater than 70° C. at atmospheric pressure which comprises, effecting reaction between methyl chloride and powdered silicon in a reactor in the presence of an effective amount of a copper-zinc-tin catalyst produced by the introduction of a mixture of powdered silicon, copper, or copper compound, zinc or zinc compound, and tin or tin compound, where the copper or copper compound, tin or tin compound, and zinc or zinc compound are introduced along with powdered silicon and methyl chloride, and the introduction of copper, tin and zinc or compounds thereof is effected at a rate sufficient to maintain in the reactor, a copper-zinc-tin catalyst having an average composition of 0.5–10% by weight copper relative to silicon, 200–3,000 ppm tin relative to copper and 0.01 part to 0.5 part and preferably 0.01 to 0.30 part of zinc per part of copper.

It is particularly preferred to practice the method of the present invention in a fluid bed reactor in a continuous manner, where silicon material having catalyst values is elutriated from the reactor and recycled.

Although methyl chloride is preferably used in the practice of the present invention, other $C_{(1-4)}$alkylchlorides, for example, ethylchloride, propylchloride, etc, also can be used.

Methyl chloride, or an inert gas such as argon, or mixture thereof, can be used to fluidize the bed of silicon particles in the reactor with or without catalyst values. The silicon present in the fluidized bed can have a particle size below 700 microns, with an average size of greater than 20 microns and less than 300 microns in size. The mean diameter of the silicon particles is preferably in the range of 100 to 150 microns.

Silicon is usually obtained at a purity of at least 98% by weight of silicon and it is then comminuted to particles of silicon in the above-described range, and is fed into an appropriate reactor as needed. Although a fluidized bed is preferred, the process of the present invention can be utilized in other types of reactors, such as fixed bed and a stirred bed. A fluidized reactor is preferably utilized since the optimum selectivity and the maximum amount of methylchlorosilane is obtained. The process of the present invention can be carried out at a temperature in the range of 250°–350° C. and more preferably at a temperature range of 260°–330° C. Reaction can occur under continuous conditions or as a batch reaction.

The expression "continuous reaction" or "continuous conditions" with respect to the description of the reaction of powdered silicon and methyl chloride in the presence of the copper-zinc-tin catalyst means that the reaction is conducted in a fluid bed reactor under continuous conditions, or in a fluid bed reactor or stirred bed reactor under simulated continuous conditions.

A fluid bed reactor, shown in FIG. 1, shows reaction under continuous conditions. FIG. 2 shows the method of the present invention employing a fluid bed reactor with a stirrer, which can be operated in a batch mode. The stirrer is employed to agitate and enhance fluidization of powdered silicon and catalyst components, such as cuprous chloride, zinc metal dust and tin powder to initiate the direct reaction between powdered silicon and methyl chloride.

If desired, a contact mass of powdered silicon, with copper-zinc-tin catalyst can be made prior to contact with methyl chloride to facilitate the generation of methylchlorosilanes. Preferably, a reactive copper compound, such as cuprous chloride, etc., can be mixed with appropriate amounts of powdered silicon, tin and zinc and heated to a temperature of about 280°–400° C.

It is also advisable to carry out the process of the present invention under a pressure of 1–10 atmospheres in instances were a fluid bed reactor is used since higher pressure increases the rate of conversion of methyl chloride to methylchlorosilanes.

Methyl chloride gas can be continuously passed through the reactor to fluidize the reaction mass and there can be passed out of the reactor, gaseous methylchlorosilanes as well as the unreacted methyl chloride. The gaseous crude product mixture and entrained reaction particulates are passed out of the fluidized reactor and passed through one or more cyclones so as to separate the larger particles of materials from the product gas stream. These particles can be returned to the reactor for further utilization in the process so as to maximize the yield of dimethyldichlorosilane from the silicon. Smaller particles are passed out with the product stream and the stream is subsequently condensed.

Purified methyl chloride is heated and recycled through the fluidized reactor for the further production of methylchlorosilanes. The crude methylchlorosilane stream is passed to a distillation train so as to distill out in essentially pure form various chlorosilane fractions produced by the process. It is necessary to distill and purify the dimethyldichlorosilane and the other chlorosilanes so that they can be utilized in the process for producing silicone materials.

Among the copper compounds which can be used to make the copper-zinc-tin catalyst or particulated silicon-copper-zinc-tin contact mass in accordance with the practice of the present invention, are carboxylic acid salts of copper such as copper formate, copper acetate, copper oxylate, etc. Copper formate is the preferred carboxylic acid salt of copper which can be further characterized as a substantially anhydrous granular material derived from technical grade cupric formate dihydrate ($Cu(CHO_2)_2.2H_2O$) or cupric formate tetrahydrate ($Cu(CHO_2)_2.4H_2O$) and exhibiting a BET surface area of from 0.5–20 $M^2$/gram by the nitrogen adsorption method.

In addition to copper carboxylic acid salts of copper, such as copper formate, there can be utilized in the practice of the invention to make the copper-zinc-tin catalyst, partially oxidized copper as the copper source. Useful sources of partially oxidized copper are taught in copending application Ser. No. 288,175, filed July 29, 1981, Ritzer et al, A Catalyst for a Process for Making Silicones. In instances where partially oxidized for cemented copper contains a level of tin relative to copper which exceeds the range required in the practice of the present invention to make the copper-zinc-tin catalyst, satisfactory results can be achieved if the reactor is purged of excess tin by employing partially oxidized copper substantially free of tin for a predetermined period of time. Further, mixtures of tin containing and partially oxidized copper substantially free of tin can be used to maintain the desired tin concentration relative to copper in practicing the method of the present invention.

One example of the preferred partially oxidized copper which can be used as the source of copper to make the copper-zinc-tin catalyst of the present invention can be characterized approximately as follows:

| | |
|---|---|
| CuO | 32-33% |
| $Cu_2O$ | 57-59% |
| Cu* | 5-10% |
| Fe | 350 ppm |
| Sn | 54 ppm |
| Pb | 22 ppm |
| Insolubles | ~0.05% |
| Bi, Ti | <20 ppm |

Additional copper materials which can be utilized in the practice of the present invention for making the catalyst, are particulated cupric chloride, cuprous chloride, particulated copper metal, etc.

Zinc metal, halides of zinc, for example zinc chloride and zinc oxide have been found effective as catalyst components. Tin metal dust (−325 ASTM mesh), tin halides, such as tin tetrachloride, tin oxide, tetramethyl tin, and alkyl tin halides also can be used as the source of tin for making the copper-zinc-tin catalyst.

The copper-zinc-tin catalyst or powdered silicon-copper-zinc-tin contact mass of the present invention can be made by introducing the above-described components into the reactor separately or as a mixture, masterbatch, alloy or blend of two or more of the various components in elemental form or as compounds or mixtures thereof.

The methyl chloride which is passed or subjected to the direct process in the fluidized bed reactor is heated to the temperature above its boiling point and passed as a gas at sufficient rate through the reactor to fludize the bed of silicon particles activated with copper-zinc-tin catalyst.

The process of the present invention can be carried out in a fluid bed reactor having a jet mill at the bottom. A suitable jet mill arrangement is shown by Dotson, U.S. Pat. No. 3,133,109, wherein large silicon particles are comminuted. The resulting finer particles of silicon and catalyst can be further used in the reactor to produce the desired alkylhalosilane.

Another method of improving silicon utilization involves abrading the surface of silicon particles. Treatment of small and large silicon particles is shown by Shade U.S. Pat. No. 4,281,149 which is assigned to the same assignee as the present invention and hereby incorporated by reference. Shade advantageously effects the removal of smaller silicon particles from the fluidized bed reactor, abrades and thereafter recycles the particles.

Another improvement is disclosed in Shah et al U.S. Pat. No. 4,307,242 which effects the selective separation of silicon fines and copper catalyst from the reactor with cyclones, classifying the particles to size and and recycling the particulate back to the reactor for further utilization.

In order that those skilled in the art will be better able to understand some of the preferred embodiments of practicing of the present invention, reference is made to the drawings which are schematics of fluid bed reactors.

FIG. 1 is a schematic of a fluid bed reactor operated under continuous conditions and providing for the fluidization of a bed of powdered silicon, means for introducing methyl chloride under pressure to fluidize such bed, a heat exchange element for controlling the temperature of the bed, means for introducing a copper source, separate means for introducing a tin and a zinc source, means for recycling silicon fines and catalyst and means for separating methychlorosilane crude.

FIG. 2 is a schematic of a fluid bed reactor which can be operated in a batch mode having a stirrer for the fluid bed which serves to facilitate the formation of a powdered silicon-copper-zinc-tin contact mass from an initial charge of powdered silicon, copper compound, such as cuprous chloride, powdered zinc metal and powdered tin metal.

More particularly, there is shown in FIG. 1, a fluid bed reactor at 10, the top of a bed of fluidized silicon at 11 which is supported by methyl chloride introduced into the reactor at ports 12, 13 and 14. Copper metal or copper compound in the form of copper oxide, copper formate, or a copper halide, such as cuprous chloride, can be continuously introduced into the fluid bed through feed pipe 15. Zinc metal or compounds thereof along with tin metal or compound, such as tin oxide, can be introduced along with makeup silicon at 16. In instances where tin is introduced in the form of a tin halide, such as tin tetrachloride, it can be introduced at 17 or along with methyl chloride at 14.

The temperature of the fluid bed is maintained at between 260°-330° C. by use of a heat exchanger through which heat transfer fluid flows through at 18 and 19. A cyclone at 20 continuously returns particulated silicon back to the reactor. Silicon fines which are not caught at cyclone 20 are conveyed by line 21 to a second cyclone 22. Fines recovered thereby are stored at 24 and 25 and returned to the reactor at 26 on a continuous basis. In instances where fines are not trapped at cyclone 22, they can be conveniently disposed at 23. Along with silicon fines, there is also returned to the reactor at line 26, catalytic amounts of copper, tin and zinc which serve to maintain the catalyst within the critical range.

There is shown more particularly in FIG. 2, a fluid bed reactor 30, having a fluid bed at 31, a supporting perforated plate at 32 through which fluidizing methyl chloride can flow, a thermocouple sensor at 33 to monitor the temperature of the fluid bed, a port at 34 for introducing powdered silicon catalyst mixture, a port at 36 for separating methylchlorosilane crude, a port at 37 for introducing methyl chloride, a thermocouple sensor at the bottom of the transmission plate to monitor the temperature of the methyl chloride, a jacketed cylinder at 40 having heating means 41 and 42, respective power means 43 and 44, and an outer jacket at 50 which serves as an insulator for heaters 41 and 42.

As previously discussed, the reaction rate constant $K_p$ establishes the crude methylchlorosilane rate. $K_p$ can be derived by rearranging and integrating the equation $$F \cdot dX = 2 \cdot R \cdot dm_{Si} \quad (1)$$

where F is methyl chloride flow (mol/hr), X is the fraction of methyl chloride reacted, and R is the rate of methylchlorosilane production in units of $$\frac{\text{moles silane}}{\text{hr, mole silicon}}.$$

and $m_{Si}$ is the moles of silicon in the reactor. Equation (1) is based on the assumption that all the crude methylchlorosilane is dimethyldichlorosilane. The resulting equation, derived by rearranging and integrating the above expression is $$\int \frac{dX}{R} = \frac{2M_{Si}}{F}. \quad (2)$$

A simplified kinetic model $$R = \frac{k_p K_A P_A}{[1 + K_B P_B]^2} \quad (3)$$

empirically derived, is found in "Organohalosilanes: Precursors to Silicones", by R. Voorhoeve, p. 229, Elsevier (1967), where $K_p$=molar reaction rate constant for silane $$\frac{\text{moles silane}}{\text{hr, mole silicon}}$$

K=adsorption equilibrium constant for MeCl (A), and silane (B), ($atm^{-1}$). In this work values of $K_A$ and $K_B$ were assumed to be $6.8\times10^{-3}$ $atm^{-1}$ and 0.4 $atm^{-1}$ respectively.

$P_A$=pressure, MeCl (atm)

$P_B$=partial pressure, silane (atm)

Equation (3) is substituted into Equation (2) which is then numerically integrated in order to obtain the mass reaction rate constant $K_p$ having units of $$\frac{\text{grams silane}}{\text{grams silicon, hr}}.$$

In order that those skilled in the art will be better able to practice the invention, the following examples are given by way of illustration and not by way of limitation. All parts are by weight.

EXAMPLE 1

A fluid bed reactor similar to that shown in FIG. 2 is set up consisting of three concentric 20 inch glass tubes having ID's of 2¾ inch, 2 inch and 1½ inch. The 1½ inch reactor tube has a distribution plate half way up the middle of the tube and a stirrer with a paddle above the distribution plate. The 1½ inch ID reactor tube is located within the 2 inch ID furnace tube having a tin oxide resistance coating and the 2 inch ID furnace tube is enclosed within the 2¾ inch ID insulating tube.

A mixture is prepared consisting of 100 parts of powdered silicon, 7.8 parts of cuprous chloride powder, 0.5 part of zinc dust and 0.005 parts of powdered tin. The powdered silicon has an average surface area of 0.5 square meters per gram, a maximum particle size of up to about 70 microns, and impurities as follows:

| Compound | Amount (ppm) |
|---|---|
| Iron | 5600 |
| Aluminum | 2700 |
| Titanium | 850 |
| Manganese | 200 |
| Calcium | 160 |

-continued

| Compound | Amount (ppm) |
|---|---|
| Nickel | 120 |

The cuprous chloride utilized in the above mixture is a substantially pure granular material of <325 ASTM mesh particle size, and containing less than 200 ppm iron and less than 20 ppm each of the following elements: Ni, Bi, Mg, Sn, Pb and Zn. The tin and zinc metal used in the above mixture have less than about 100 ppm of metallic and non-metallic impurities. The mixture of silicon powder and catalyst ingredients is fed into the above-described reactor at a temperature of about 300° C. with methyl chloride flowing upward through the distribution plate and the stirrer is operated to agitate the fluid bed. After a period of about 5 minutes of agitation of the fluid bed, there is formed about 3.0 part silicon tetrachloride and lesser amounts of perchlorinated polysilanes per part of cuprous chloride used as shown by volatiles resulting from the reaction between cuprous chloride and the silicon powder, which are captured with a condenser and analyzed by gas chromatography.

The direct reaction between the powdered silicon and methyl chloride in the presence of the resulting powdered silicon copper-zinc-tin contact mass is allowed to continue until approximately 40% of the silicon is reacted at 300° C. During the course of the reaction, methylchlorosilane crude is continuously condensed and periodically sampled and weighted. $K_p$ is calculated and T/D and % residue are determined by gas chromatography. In one series of reactions, the effect of tin on rate (grams of silane per gram of silicon per hour) and selectivity is determined at 300° C. with mixtures having a ratio of zinc to copper maintained at 0.10, while the ratio of ppm of tin to copper is varied over a range of 0–3,000. The following are the approximate results obtained, where the % copper as defined above is based on weight of silicon:

TABLE I

THE EFFECT OF TIN ON RATE AND SELECTIVITY
Runs at 300° C., Zn/Cu = 0.10

| Sn/Cu (ppm) | % Cu | Rate* ($K_p$) | % Residue** | T/D** |
|---|---|---|---|---|
| 0 | 5 | 16 | 2.1 | 0.09 |
| 420 | 5 | 33 | 1.4 | 0.06 |
| 1000 | 5 | 84 | 1.3 | 0.06 |
| 1500 | 5 | 106 | 1.6 | 0.05 |
| 2200 | 5 | 132 | 2.1 | 0.06 |
| 3000 | 5 | 194 | 6.4 | 0.05 |
| 1000 | 1.5 | 32 | 1.9 | 0.06 |
| 3000 | 1.5 | 75 | 5.2 | 0.04 |

*values obtained at 20% silicon utilization
**cumulative values up to 40% silicon utilization Different runs under substantially similar conditions over a Sn/Cu ppm range of 0 to 5,000, provides a $K_p$ of 16 to 331, a % residue of 1.6 to 6.4 and a T/D of 0.060 to 0.073. At 1.5% Cu, there is obtained over a 1000 to 3000 Sn/Cu ppm range, a 29 to 75 $K_p$, a 2.3 to 5.2% residue and a 0.039 to 0.037 T/D.

An additional series of runs are made to determine selectivity and rate for a catalyst having a ratio of zinc to copper over a range of 0 to 0.60, while maintaining a concentration of 1000 ppm of tin, relative to copper. The following are the approximate results obtained:

TABLE II

| THE EFFECT OF Zn/Cu Ratio ON RATE AND SELECTIVITY (1000 ppm Sn/Cu) | | | | |
|---|---|---|---|---|
| Zn/Cu | % Cu | T/D** | Rate* ($K_\rho$) | % Residue** |
| 0 | 5 | 0.14 | 46 | 2.1 |
| 0.02 | 5 | 0.06 | 50 | 3.1 |
| 0.05 | 5 | 0.04 | 72 | 2.3 |
| 0.10 | 5 | 0.05 | 84 | 1.3 |
| 0.14 | 5 | 0.05 | 61 | 0.6 |
| 0.20 | 5 | 0.06 | 83 | 2.2 |
| 0.25 | 5 | 0.07 | 81 | 1.6 |
| 0.38 | 5 | 0.09 | 84 | 1.4 |
| 0.50 | 5 | 0.05 | 75 | 1.3 |
| 0.60 | 5 | 0.10 | 78 | 2.0 |

*measured at 20% silicon utilization
**measured at 40% silicon utilization

A continuation of the same series is made under substantially similar conditions using 1.5% by weight copper based on silicon:

TABLE IIA

| Zn/Cu | % Cu | T/D** | Rate* ($K_\rho$) | % Residue** |
|---|---|---|---|---|
| 0.006 | 1.5 | 0.062 | 35 | 2.4 |
| 0.011 | 1.5 | 0.052 | 58 | 3.1 |
| 0.017 | 1.5 | 0.046 | 76 | 2.1 |
| 0.022 | 1.5 | 0.041 | 48 | 3.3 |
| 0.048 | 1.5 | 0.042 | 51 | 2.4 |
| 0.054 | 1.5 | 0.056 | 38 | 1.8 |
| 0.25 | 1.5 | 0.099 | 53 | 1.9 |

*measured at 20% silicon utilization
**measured at 40% silicon utilization

A further series of reactions are conducted to determine the effect of the copper concentration on rate and selectivity at temperatures of about 300° C. The following are the approximate results obtained:

TABLE III

| EFFECT OF COPPER CONCENTRATION ON RATE AND SELECTIVITY | | | | | |
|---|---|---|---|---|---|
| % Cu | Zn/Cu | Sn/Cu ppm | Rate* ($K_\rho$) | T/D* | % Residue* |
| 1.5 | 0.05 | 1000 | 51 | 0.042 | 2.4 |
| 1.5 | 0.05 | 1000 | 38 | 0.056 | 1.8 |
| 5 | 0.05 | 1000 | 174 | 0.037 | 1.7 |
| 5 | 0.05 | 1000 | 69 | 0.041 | 0.7 |
| 5 | 0.10 | 420 | 46 | 0.045 | 1.3 |
| 10 | 0.10 | 420 | 143 | 0.067 | 1.7 |

*measured at 20% silicon utilization

With the exception of the 0% Cu run, Table IV below is a consolidation of Tables I–III and some of the above data. It shows the approximate effects of the presence or complete absence of various combinations of copper, zinc and tin on rate and selectivity with respect to methylchlorosilane production resulting from the reaction of powdered silicon and methyl chloride.

TABLE IV

| EFFECTS OF COPPER, TIN, AND ZINC ON RATE AND SELECTIVITY | | | | | |
|---|---|---|---|---|---|
| % Cu | % Zn | % Sn | Rate | T/D | Residue |
| 0 | 0.05 | 0.005 | 0 | — | — |
| 5 | 0 | 0 | 13 | 0.21 | 1.9 |
| 5 | 0.5 | 0 | 16 | 0.060–.090 | 1.6–1.9 |
| 5 | 0 | 0.005 | 46 | 0.11–.12 | 2.2–2.4 |
| 5 | 0.5 | 0.005 | 84–107 | 0.05–.057 | 1.3–1.4 |

The above results show that the copper-zinc-tin catalyst of the present invention provides a surprising rate improvement, while selectivity is also substantially improved with respect to dimethyldichlorosilane production as compared to the use of a copper catalyst alone, or a copper catalyst promoted with zinc or tin alone.

EXAMPLE 2

A 1 inch stirred bed reactor was set up. The stirred bed reactor consisted of a stainless steel tube approximately 18 inches long with a 1 inch ID. It was equipped with dual zone electrical heaters to provide a reaction zone of about 1"×6". It was also equipped with a helical stainless steel stirrer.

The stirred bed reactor was preheated to 300° C. under a purge of nitrogen until stabilized. The reactor was then charged with a mixture of powdered silicon as utilized in Example 1, 5% by weight thereof of copper, utilized in the form of partially oxidized copper, 0.5% by weight of zinc, based on the weight of copper, and 500 ppm of tin per part of copper. The partially oxidized copper had the following approximate composition:

| | |
|---|---|
| CuO | 32–33% |
| $Cu_2O$ | 57–59% |
| Cu* | 5–10% |
| Fe | 350 ppm |
| Sn | 54 ppm |
| Pb | 22 ppm |
| Insolubles | ~0.05% |

More particularly, there was charged to the stirred bed reactor, a mixture of 50 parts of powdered silicon, 2.9 parts of copper oxide, 0.25 part of zinc metal and 0.0015 part of tin metal. The mixture had been blended together and added to the stirred bed reactor at a temperature of 300° C. An equal molar mixture of dimethyldichlorosilane and methyl chloride was then introduced into the stirred bed reactor to pretreat the charge. The dimethyldichlorosilane-methyl chloride flow was then terminated when the charge had been treated with sufficient dimethyldichlorosilane to provide a ratio of moles of dimethyldichlorosilane to copper having a value of at least 3. Methyl chloride was then introduced into the reactor at a feed rate of 12.5 parts per hour. Reaction was terminated after 16 hours and the following rate and selectivity results were obtained:

TABLE V

| | |
|---|---|
| $K_\rho$ | 65–75 |
| T/D | 0.07–0.08 |
| % Residue | 4–5 |

The above results show that the copper-zinc-tin catalyst of the present invention resulting from the use of partially oxidized copper as the source of copper can be used to provide dimethyldichlorosilane under simulated continuous conditions at a satisfactory production rate while maintaining a satisfactory degree of selectivity.

EXAMPLE 3

Silicon powder having an average particle size of greater than about 20 microns and less than about 300 microns is fluidized in a fluid bed reactor with methyl chloride which is continuously introduced at a pressure of from about 1 to about 10 atmospheres. The temperature of the reactor is maintained at about 250° C. to 350° C. Partially oxidized copper of Example 2 is continuously introduced at a rate sufficient to maintain from about 0.5% to about 10% by weight of copper based on the weight of fluidized silicon. Tin tetrachloride is introduced into the fluid bed reactor at least periodically at a rate sufficient to maintain a tin concentration of about 200–3,000 ppm of tin based on the weight of copper. A mixture of zinc metal dust and powdered silicon is laterally introduced into the fluid bed reactor at a rate sufficient to maintain a ratio of zinc to copper having a value of from about 0.01 to 0.25 part of zinc per part of copper.

Along with the introduction of tin tetrachloride and zinc metal, elutriated silicon containing material having copper-zinc-tin catalyst values and in the form of an average particle size of about 2 to 50 microns and containing a mixture of particulated silicon, copper, tin and zinc are at least periodically recycled into the fluid bed.

During the course of the continuous run, a sample of the reaction bed is obtained and analyzed by atomic absorption. It is found that the bed contains about 2% by weight of copper based on the weight of fluidized silicon, 0.08 part of zinc and 0.001 part of tin per part of copper. The following average results are obtained over a period of 96 hours of continuous operation:

TABLE VI

| $K_p$* | T/D | % Residue |
|---|---|---|
| 20–40 | 0.07–0.10 | 4–5% |

*reference to 300° C. at 1 atmosphere

The above $K_p$ value, T/D ratio and % residue shows that the copper-zinc-tin catalyst of the present invention can provide a satisfactory dimethyldichlorosilane production rate while maintaining a high degree of selectivity under continuous reaction conditions in a fluid bed reactor.

EXAMPLE 4

A mixture of 100 parts of silicon powder, 7.8 parts of cuprous chloride, 0.005 part of tin powder and 0.5 part of zinc dust was thoroughly blended together. The mixture was then placed in a furnace maintained above 300° C. and purged with argon. The mixture was not agitated and was left in the furnace until reaction between the copper salt and silicon was complete. The completion of the reaction was shown by a cessation of the formation of silicon tetrachloride. Based on this method of preparation, there was produced a contact mass of powdered silicon-copper-zinc-tin having 5% by weight of copper metal based on the weight of silicon, 0.1 part of zinc per part of copper and 1000 ppm of tin per part of copper.

The contact mass was charged to a 1½ inch inside diameter fluidized bed reactor. The temperature was raised to 300° C. and methyl chloride flow was initiated. A condenser downstream of the reactor was used to recover crude chlorosilane products. The rate of crude production was determined by weighing recovered crude over predetermined time intervals. The composition of the crude was determined by gas chromatography. The following results were obtained after about 20% of the silicon has been reacted which was also approximately the same results achieved after 80–90% of the silicon had been utilized.

| % Copper | Sn/Cu (ppm) | Zn/Cu | $K_p$ | T/D | % Residue |
|---|---|---|---|---|---|
| 5 | 1000 | 0.10 | 84 | 0.052 | 1.3 |

The above results show that the beneficial effects of the copper-zinc-tin catalyst of the present invention can be realized when present with powdered silicon as a preformed contact mass for the production of dimethyldichlorosilane.

Although the above examples are directed to only a few of the very many variables which can be utilized in the practice of the present invention, it should be understood that the present invention is directed to the use of a much broader variety of copper compounds, tin compounds and zinc compounds, reaction conditions and types of reactors which preferably is a fluidized bed reactor operated under continuous conditions but which also can include stirred bed reactors, fixed bed reactors and fluid bed reactors operated in a batch mode as set forth in the description preceding these examples.

What we claim as new and desire to secure by Letters Patent of the United States is:

1. A method for making alkylhalosilanes comprising effecting reaction between an alkyl halide and powdered silicon in the presence [of an effective amount] of a copper-zinc-tin catalyst *wherein the catalyst has relative weights of tin to copper and zinc to copper and copper to silicon which are selected to substantially enhance the rate of dialkyldihalosilane formation, while substantially reducing the weight ratio of alkyltrihalosilane to dialkyldihalosilane and maintaining or reducing the weight percent of residue in the crude reaction product.*

2. A method in accordance with claim 1, wherein the alkyl halide is methyl chloride.

3. A method in accordance with claim 1, which is practiced under continuous conditions in a fluid bed reactor.

4. A method in accordance with claim 1, which is practiced in a stirred bed reactor.

5. A method in accordance with claim 1, which is practiced in a fixed bed reactor.

6. A method in accordance with claim 1, which is operated in a batch mode.

7. A method in accordance with claim 1, which is practiced at a temperature in the range of 250°–350° C.

8. A method in accordance with claim 1, where the copper-zinc-tin catalyst comprises from 0.5–10% by weight of copper relative to silicon and 200–3000 ppm of tin and 0.01 part to 0.5 part of zinc, per part of copper.

9. A method in accordance with claim 1, where partially oxidized copper is used as the source of copper for the powdered copper-zinc-tin catalyst.

10. A method in accordance with claim 1, where cuprous chloride is used as the source of copper for the copper-zinc-tin catalyst.

11. A method in accordance with claim 1, where tin tetrachloride is used as the source of tin for the copper-zinc-tin catalyst.

12. A method in accordance with claim 1, using a contact mass of powdered silicon and copper-zinc-tin catalyst.

13. A method in accordance with claim 1, where zinc metal is used as the source of zinc for the copper-zinc-tin catalyst.

14. A method in accordance with claim 1, where zinc chloride is used as the source of zinc for the copper-zinc-tin catalyst.

15. A method in accordance with claim 1, where zinc oxide is used as the source of zinc for the copper-zinc-tin catalyst.

16. A method in accordance with claim 1, where tin metal dust is used as the source of tin for the copper-zinc-tin catalyst.

17. A method in accordance with claim 1, where tin oxide is used as the source of tin for the copper-zinc-tin catalyst.

18. A method in accordance with claim 1, where tetramethyl tin is used as the source of tin for the copper-zinc-tin catalyst.

19. A method in accordance with claim 1, where an alkylhalo tin compound is used as the source of tin for the copper-zinc-tin catalyst.

20. A method in accordance with claim 1, where copper formate is used as the source of copper for the copper-zinc-tin catalyst.

21. A method for making methylchlorosilanes which substantially enhances the rate of dimethyldichlorosilane formation, while substantially reducing the weight ratio of methyltrichlorosilane to dimethyldichlorosilane, and maintaining or reducing the percent by weight of products in the resulting methylchlorosilane crude having a boiling point of greater than 70° C. at atmospheric pressure which comprises, effecting reaction between methyl chloride and powdered silicon in a reactor in the presence of an effective amount of a copper-zinc-tin catalyst produced by the introduction of a mixture of powdered silicon, copper, or copper compound, zinc or zinc compound, and tin or tin compound, where the copper or copper compound, tin or tin compound, and zinc or zinc compound are introduced along with powdered silicon and methyl chloride, and the introduction of copper, tin and zinc or compounds thereof is effected at a rate sufficient to maintain in the reactor, a copper-zinc-tin catalyst having an average composition of 0.5–10% by weight copper relative to silicon, 200–3,000 ppm tin relative to copper and 0.01 part to 0.5 part of zinc per part of copper.

22. A method in accordance with claim 21, where the average composition of the copper-zinc-tin catalyst is maintained by conducting the reaction between methyl chloride and powdered silicon in a fluid bed reactor under continuous conditions and copper, zinc and tin or compounds thereof are continuously recycled as elutriated material along with powdered silicon to the reactor.

23. A method in accordance with claim 21, utilizing partially oxidized copper as the source of copper for the copper-zinc-tin catalyst, where the partially oxidized copper has less than 2000 ppm of tin based on the weight of copper which allows for the use of partially oxidized copper as the source of copper for the copper-zinc-tin catalyst having a level of tin exceeding the ppm range based on the weight of copper needed to maintain the copper-zinc-tin catalyst.

24. A powdered silicon-copper-zinc-tin contact mass comprising 0.5–10% by weight copper based on silicon, 200–3000 ppm of tin per part of copper and 0.01 part to 0.5 part of zinc per part of copper.

25. A method for making a contact mass of claim 24 comprising heating a mixture of powdered silicon cuprous chloride, tin and zinc or compounds thereof at a temperature in the range of from 280°–400° C. until the generation of silicon tetrachloride ceases.

26. A copper-zinc-tin catalyst useful for making [methyl chlorosilanes] *alkylhalosilanes* based on the reaction between [methylchloride] *an alkylhalide* and powdered silicon *having relative weights of tin to copper and zinc to copper selected to substantially enhance the rate of dialkyldihalosilane formation, while substantially reducing the weight ratio of alkyltrihalosilane to dialkyldihalosilane and maintaining or reducing the weight percent of residue in the crude reaction product.*

27. A method for making methylchlorosilanes which substantially enhances the rate of dimethyldichlorosilane formation while substantially reducing the weight ratio of methyltrichlorosilane to dimethyldichlorosilane and maintaining or reducing the percent by weight of products in the resulting methylchlorosilane crude having a boiling point of greater than 70° C. at atmospheric pressure, which comprises effecting reaction between methyl chloride and powdered silicon in the presence of an effective amount of a copper-zinc-tin catalyst where the copper-zinc-tin catalyst comprises from 0.5 to 10% by weight of copper relative to silicon and 200–3000 ppm of tin and 0.01 part to 0.5 part of zinc per part of copper.

28. A method in accordance with claim 27 where partially oxidized copper is used as a source of copper for the copper-zinc-tin catalyst.

*29. The copper-zinc-tin catalyst of claim 26 having, by weight, 200–3000 ppm of tin relative to copper and 0.01 to 0.5 part of zinc per part of copper.*

*30. A copper-zinc-tin catalyst useful for making methylchlorosilanes based on the reaction between methylchloride and powdered silicon having relative weights of tin to copper and zinc to copper selected to substantially enhance the rate of dimethyldichlorosilane formation, while substantially reducing the weight ratio of methyltrichlorosilane to dimethyldichlorosilane and maintaining or reducing the weight percent of residue in the crude reaction product.*

*31. The copper-zinc-tin catalyst of claim 30 having, by weight, 200–3000 ppm of tin relative to copper and 0.01 to 0.5 part of zinc per part of copper.*

*32. A method for making methylchlorosilanes comprising effecting reaction between methylchloride and powdered silicon in the presence of a copper-zinc-tin catalyst wherein the catalyst and the powdered silicon form a powdered silicon-copper-zinc-tin contact mass comprising, by weight, 0.5–10% copper based on silicon, 200–3000 ppm tin relative to copper and 0.01 part to 0.5 part of zinc per part of copper.*

* * * * *